US009119612B2

(12) United States Patent
Buressiniani

(10) Patent No.: US 9,119,612 B2
(45) Date of Patent: Sep. 1, 2015

(54) DEVICE FOR TRANSCUTANEOUS BIOPSY

(76) Inventor: Odoardo Buressiniani, Rome (IT)

( * ) Notice: Subject to any disclaimer, the term of this patent is extended or adjusted under 35 U.S.C. 154(b) by 919 days.

(21) Appl. No.: 12/594,835

(22) PCT Filed: Apr. 7, 2008

(86) PCT No.: PCT/IB2008/000827
§ 371 (c)(1),
(2), (4) Date: Jan. 27, 2010

(87) PCT Pub. No.: WO2008/122870
PCT Pub. Date: Oct. 16, 2008

(65) Prior Publication Data
US 2010/0160827 A1 Jun. 24, 2010

(30) Foreign Application Priority Data

Apr. 6, 2007 (IT) .............. RM2007A0196

(51) Int. Cl.
A61B 10/02 (2006.01)
A61B 17/32 (2006.01)
(52) U.S. Cl.
CPC ........... *A61B 10/0275* (2013.01); *A61B 10/025* (2013.01); *A61B 10/0266* (2013.01); *A61B 2010/0258* (2013.01); *A61B 2017/32004* (2013.01); *A61B 2017/320064* (2013.01)
(58) Field of Classification Search
CPC ............. A61B 10/025; A61B 10/0266; A61B 2010/0258; A61B 2017/320064
USPC .......... 600/562–568; 606/167, 170, 176, 179, 606/180, 184, 185
See application file for complete search history.

(56) References Cited

U.S. PATENT DOCUMENTS

| 3,605,721 | A | 9/1971 | Hallac |
| 4,785,826 | A | 11/1988 | Ward |
| 5,634,473 | A * | 6/1997 | Goldenberg et al. ......... 600/567 |
| 5,885,226 | A * | 3/1999 | Rubinstein et al. ........... 600/564 |
| 6,015,391 | A | 1/2000 | Rishton et al. |
| 2007/0142743 | A1* | 6/2007 | Provencher et al. .......... 600/562 |
| 2008/0154150 | A1* | 6/2008 | Goldenberg ................... 600/564 |

FOREIGN PATENT DOCUMENTS

| EP | 1 136 039 A2 | 9/2001 | |
| WO | WO 2005/013831 | * 2/2005 | ............ A61B 10/00 |
| WO | WO2005/013831 A2 | 2/2005 | |

* cited by examiner

*Primary Examiner* — Lee S Cohen
*Assistant Examiner* — Emily Lloyd
(74) *Attorney, Agent, or Firm* — Laubscher, Spendlove & Laubscher, P.C.

(57) ABSTRACT

A biopsy device includes a first hollow cylindrical element, a second hollow cylindrical element inside which the first hollow cylindrical element is insertable and a locking element that is suitable for locking a tissue sample inside the first hollow cylindrical element. The locking element includes a deformable portion of the first hollow cylindrical element that is able to become deformed to enable a cross section of the first hollow cylindrical element to be closed, the deformable portion connecting a distal end of the first hollow cylindrical element to a body of the first hollow cylindrical element.

6 Claims, 7 Drawing Sheets

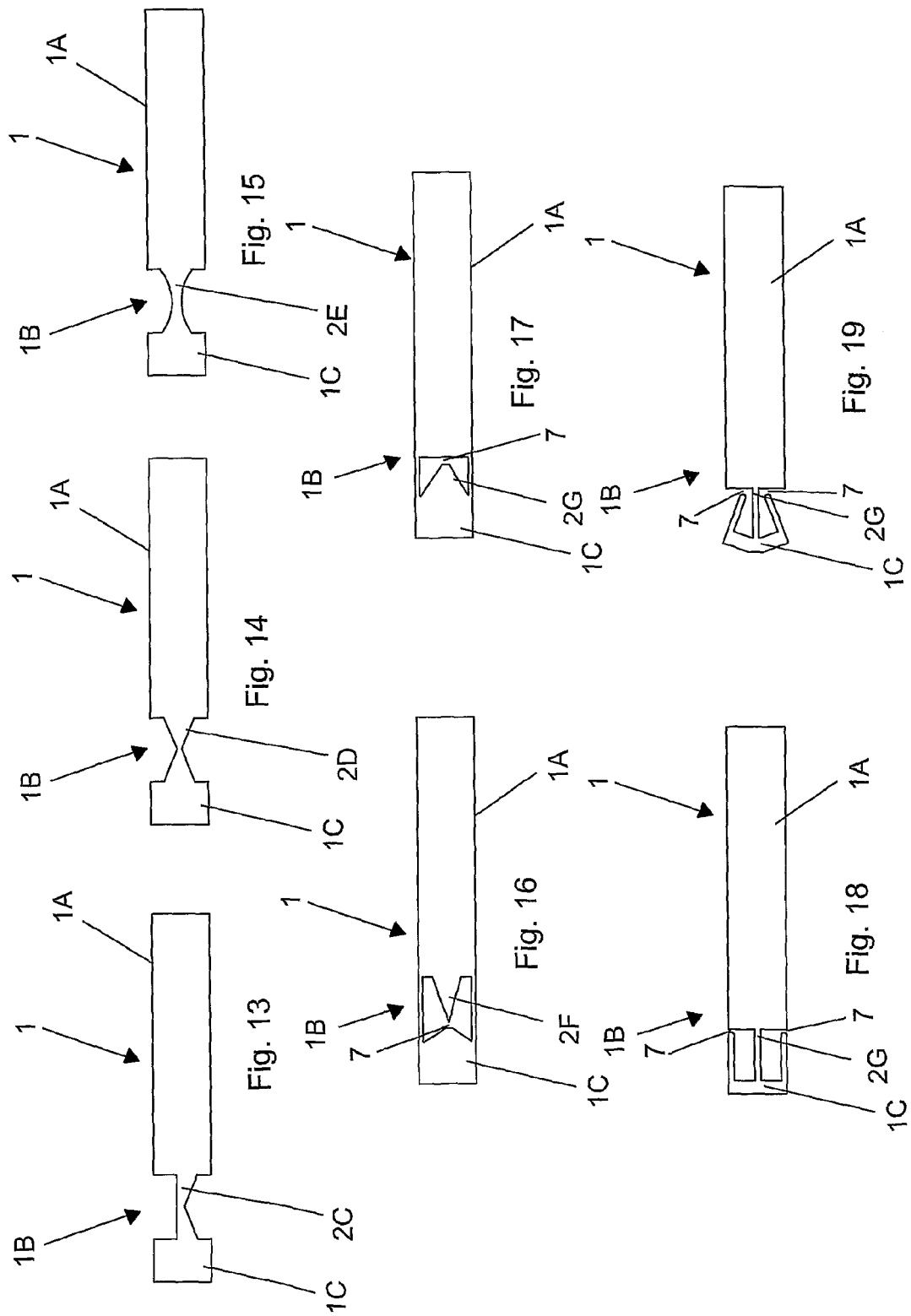

DEVICE FOR TRANSCUTANEOUS BIOPSY

This application is a national phase of PCT International Application No. PCT/IB2008/000827 filed Apr. 7, 2008. PCT/IB2008/000827 claims priority to IT Application No. RM2007A000196 filed Apr. 6, 2007. The entire contents of these applications are incorporated herein by reference.

BACKGROUND OF THE INVENTION

The present invention relates to a transcutaneous biopsy device for both soft tissue and bone marrow tissue, which is also known as rigid tissue, in particular the present invention relates to a device for taking samples of organic tissue from the body of a patient.

BRIEF DESCRIPTION OF THE PRIOR ART

In the prior art needle devices are known for the transcutaneous biopsy of rigid tissue, comprising a needle in the shape of a hollow cylinder, with a variable diameter and length, an end of which, said proximal end, is provided with a grip suitable for enabling the operator to manoeuvre the needle, whilst the other end said distal end, is provided with a cutting edge that is suitable for enabling the sample of tissue to be taken to be separated at least partially from the surrounding tissue.

The needle is generally coupled with a spindle consisting of a steel rod of dimensions such as to be able to slide inside the needle. Said rod is provided with a sharpened end that protrudes from the distal end of the needle and is intended for perforating the particularly hard surface layer of the bone tissue to reach the marrow tissue.

The biopsy is conducted by pushing and rotating the needle through the skin and the muscle bundles of the patient until the sharp end of the spindle reaches the bone and perforates the surface layer, reaching the marrow tissue.

At this point the spindle is extracted from inside the hollow needle and the needle is pushed further, advancing and rotating inside the marrow tissue, so that the cutting distal end of the needle isolates an approximately cylindrical portion of tissue from the surrounding tissue and surrounds the approximately cylindrical portion in the interior thereof: this portion of the tissue constitutes the bioptic sample to be taken. The aforesaid sample remains connected to the surrounding tissue at the distal end thereof, i.e. at the end facing the outside of the needle.

At this point, in order to cause the sample to be detached, the so-called dislocation step is performed that essentially consists of performing rotation and oscillation of the needle in a direction that is substantially perpendicular to the longitudinal axis thereof; after performing this manoeuvre and then after causing the sample to detach completely at the distal end thereof the needle is extracted from the patient.

This manoeuvre in general creates significant trauma for the patient, inasmuch as the oscillating movements impressed on the needle cause numerous microfractures to the bone tissue, which cause considerable suffering in the patient and extend healing time thereof.

Further, there is no guarantee that after this manoeuvre has been performed the sample will actually be taken. It is in fact possible that the distal part of the sample has not been completely detached from the surrounding tissue and that therefore, during extracting of the hollow needle, it remains inside the body, or that although complete detachment of the sample from the surrounding tissue has been obtained there is a distal portion of the sample that partially protrudes from the distal end of the needle, during extraction this portion may become damaged or facilitate the total loss of the sample, inside the body; in both the disclosed situations it is necessary to repeat the sampling operation, with consequent significant deterioration of the trauma and of the suffering caused to the patient.

Devices are further known for transcutaneous biopsy of rigid tissues, comprising a needle and a spindle with the same features as those disclosed previously, in which the needle is tapered at the distal end thereof.

These devices comprise locking elements to be inserted slidingly through the proximal part of the needle, after the latter has been inserted into the body of the patient and the interior thereof encloses a tissue sample to be taken.

These locking elements are shaped so as to be able to be inserted between a zone of the internal wall of the needle and the tissue sample comprised therein.

When the locking element is pushed as far as the tapered end portion of the hollow cylinder it is deflected radially to the inside so as to force the tissue sample against the opposite internal wall zone of the hollow needle.

This causes a certain sample locking force to be created between a part of the locking element and the internal wall of the needle.

This locking force, during the needle-extracting step, avoids the dislocation manoeuvre disclosed previously; it is possible to obtain complete detachment of the sample at the distal end thereof from the surrounding tissues by rotation of the needle, preventing oscillations that create the aforementioned microfractures in the bone tissue. Nevertheless, this type of device has significant drawbacks.

Inserting the needle-locking element is very delicate as it can often damage the penetrated sample at the distal end of the needle, through crushing or rubbing; the removed but damaged tissue may create artefacts during clinical evaluation thereof and so the patient is forced to undergo again a biopsy with consequent significant deterioration of the trauma and of the suffering caused.

The locking force that is created through the effect of the friction between the sample, the locking element and the internal wall of the hollow needle may not be sufficient to clamp the sample. In these situations the effect of the rotations given to the needle may not have the hoped-for effect and it may therefore be impossible to take the sample. Another negative condition that may occur due to insufficient locking force is the loss of the sample from the internal cavity of the needle during extracting. In this situation it is possible to lose the sample inside the tissues that the hollow needle passes through before being removed.

Evaluating a correct locking force would necessarily require having to know exactly the nature of the sample, defined as physical and mechanical features of the organic tissue, and above all the surrounding conditions that obtain near the tissue to be removed such as greater or lesser blood flow. The combination of a particular tissue with greater or lesser blood flow may cause a greater or lesser friction coefficient between the sample, the walls of the locking element and the walls of the needle, creating greater or lesser friction force and thus a greater or lesser locking force. If during a biopsy the locking force is insufficient, the result is the failure to take the sample, which implies, as already said, having to repeat the operation and thus a situation of further discomfort for the patient.

From the prior art other devices are known consisting of a needle, a spindle and a locking element with the latter, having peculiar features that attempt to resolve in part the disclosed difficulties.

Some devices exploit exactly the same operating principle disclosed above, with the sole teaching of having the locking element reinserted inside the hollow needle, in this way, the risk of damaging the tissue sample contained inside the needle is avoided, but all the other disclosed drawbacks remain.

Often, in order to increase locking force and thus increase the percentages of successful sampling, the locking element may have the distal end shaped as a coil and can be provided with an independent driving arrangement. Once the tissue sample has been introduced inside the needle, it is possible to tighten the distal zone of the spiral-shaped locking element by a driving arrangement connected to the locking element, in this way friction force is created between the tissue and the distal part of the locking element. This solution, like many others similar thereto, can on the one hand ensure greater clamping, reducing but not eliminating the risks disclosed above. On the other hand it increases the risk of spoiling the sample in the locking step. In fact, a spiral shape or other geometrical shapes that are similar thereto can cause damage to the sample distributed over all the surface thereof, which leads, as already said, to a series of artifacts being obtained during the clinical valuation step and then to the biopsy being consequently repeated.

From the prior art needles are known for transcutaneous biopsy on soft tissues such as, for example, pulmonary tissue, tissue constituting organs such as the prostrate, the liver, etc. These devices consist of a spindle that is substantially cylindrical to the end of the tip from which a housing is obtained—for example by obtaining a levelling along a portion of the spindle—suitable for receiving the sample to be taken, and of a hollow needle with a cutting tip, slidingly coupled outside said spindle.

The housing has dimensions such as to receive a tissue sample of a sufficient size for the histological examinations to be conducted thereupon.

In order to conduct the biopsy, the instrument is introduced into the body of the patient with the spindle retracted inside the hollow needle so that only the tip protrudes therefrom.

When the tip of the spindle has reached the zone of the body of the patient from which the sample has to be taken, the spindle is made to exit the needle by reciprocal axial sliding. In this way, a portion of tissue surrounding the spindle rests on the housing obtained on the spindle.

At this point the hollow needle is moved until it covers said housing so that the cutting tip of the hollow needle separates from the surrounding tissue, with a guillotine action, the portion of tissue that has penetrated into the aforesaid housing.

These needles have the drawback that a sufficient quantity of tissue does not always enter the aforesaid housing for a bioptic examination, so the taking of the tissue sample often has to be repeated, with consequent discomfort for the patient.

SUMMARY OF THE INVENTION

The present invention proposes providing a device for transcutaneous biopsy of both hard and soft tissues, which is completely free of all the aforesaid drawbacks and which enables the suffering of the patient to be minimized who has to submit a bioptic intervention.

According to the present invention a biopsy device is provided, comprising a first hollow cylindrical element, a second hollow cylindrical element inside which the first hollow cylindrical element is insertable and a locking element that is suitable for locking a tissue sample inside the first hollow cylindrical element, wherein the locking element comprises a deformable portion of the first hollow cylindrical element, that is able to become deformed to enable a cross section of the first hollow cylindrical element to be closed, said deformable portion being arranged near a distal end of the first hollow cylindrical element.

This closure ensures secure and complete detachment both of a soft tissue sample and a bone-marrow tissue sample, that is inside said second hollow cylindrical element, eliminating the risks of damage to the sample. Conceptually, compared with what is described and present in the prior art, this locking element does not intend to exploit the friction force between the tissue and the walls thereof as a clamping force, but acts in a mechanical manner, simply reducing to zero a zone of the tissue entry section.

BRIEF DESCRIPTION OF THE FIGURES

The invention can be better understood and implemented with reference to the following description that is given purely by way of non-limiting example, and with reference to the attached drawings, in which:

DETAILED DESCRIPTION

Figure 1:
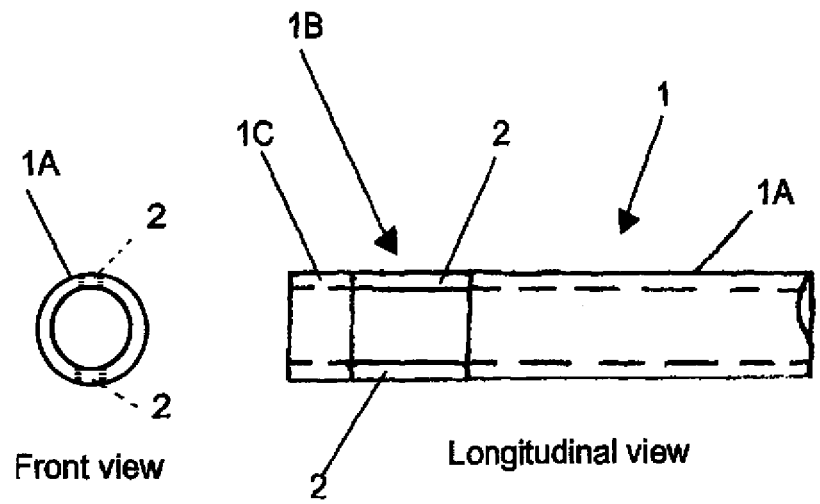

FIG. 1 shows a longitudinal and frontal view of a first hollow cylindrical element 1 of a biopsy device according to the invention. The first hollow cylindrical element 1 comprises a body 1A having a distal end 1C connected to the body 1A by a deformation portion 1B shaped in such a manner as to obtain a pair of ribs 2 constituting a locking element, that through deformation closes a cross section of the first hollow cylindrical element 1.

Figure 2:
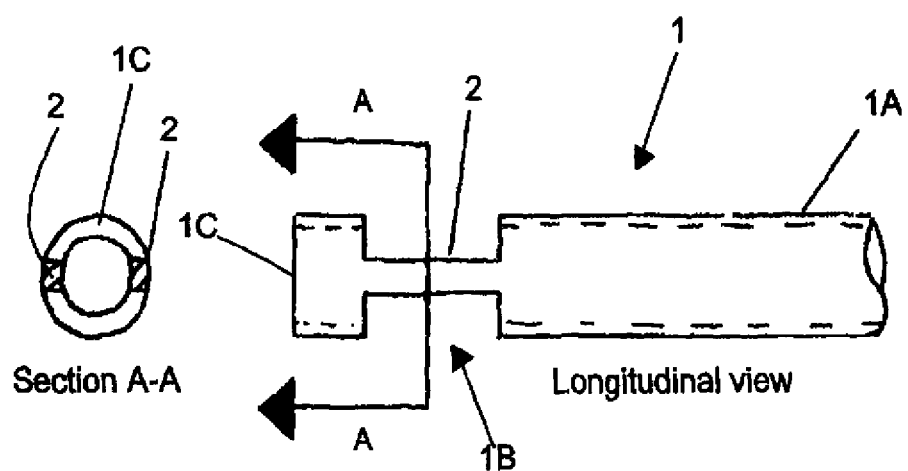
Figure 3:
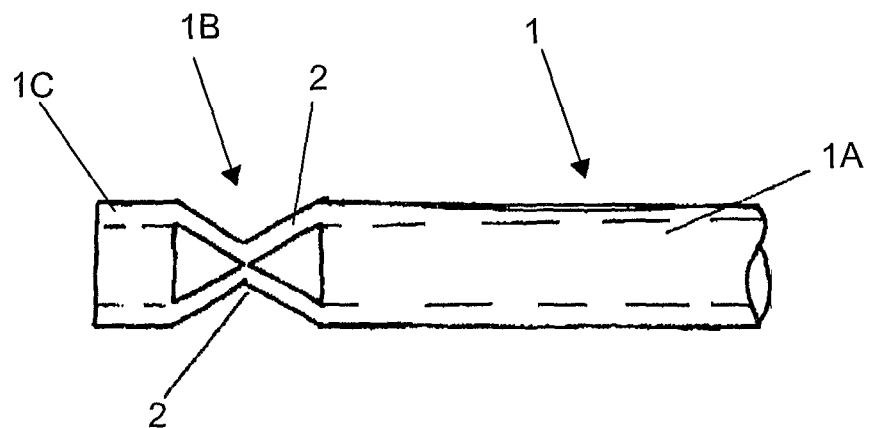

FIG. 2 shows another longitudinal view of the first hollow cylindrical element and a section of the distal end of the first hollow cylindrical element;

FIG. 3 is a longitudinal view of the first hollow cylindrical element 1, with the ribs 2 of the deformation portion 1B in a deformed configuration in which they enclose a cross section of the first hollow cylindrical element 1.

Figure 4:
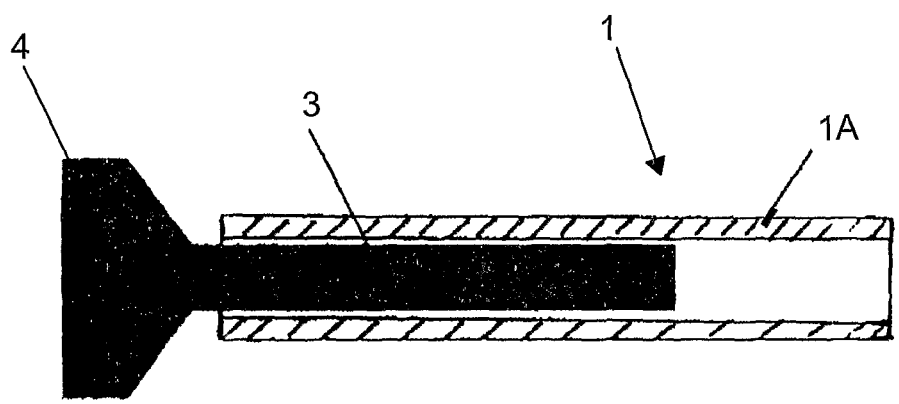
Figure 5:
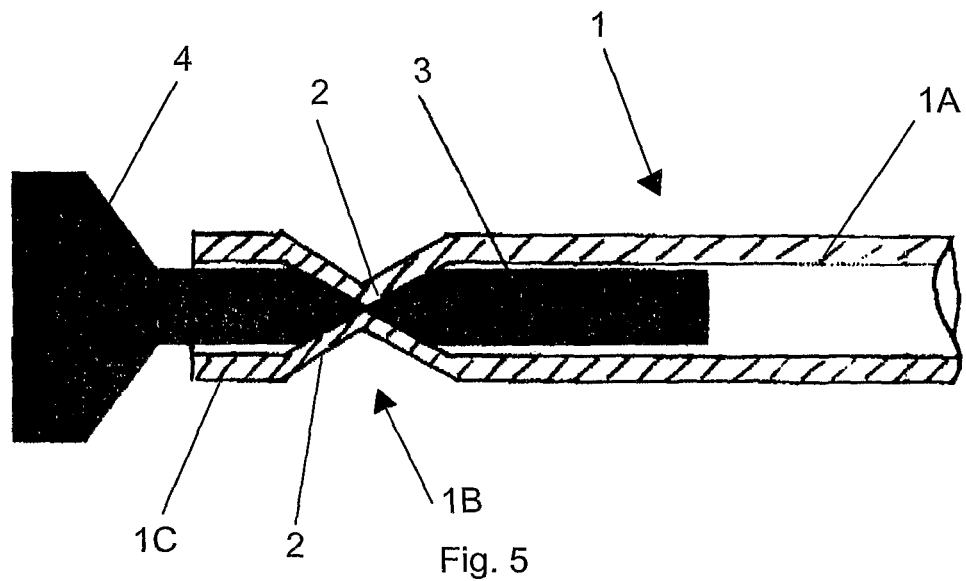

FIG. 4 is a longitudinal section of the first hollow cylindrical element, showing a tissue sample the distal end of which is still connected to the surrounding tissues;

FIG. 5 is a longitudinal section of the first hollow cylindrical element 1 inside which a tissue sample 3 has been enclosed and to which deformation portion 1B a compressive deforming force has been applied that has placed the ribs 2 in the deformed configuration, in which the detachment of the tissue sample 3 is obtained in the closing zone of the cross section of the first hollow cylindrical element 1.

Figure 6:
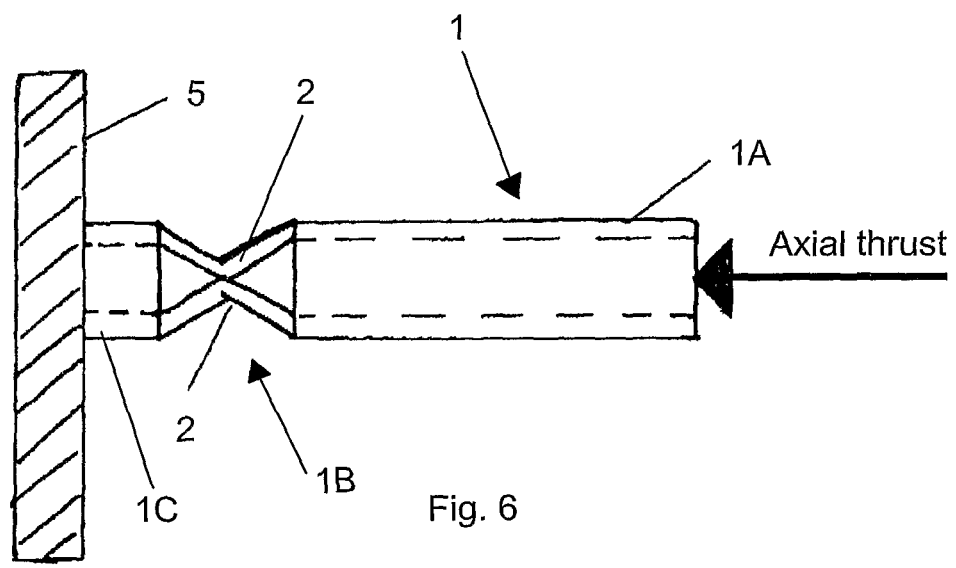

FIG. 6 is a schematic view that illustrates the way in which the ribs 2 of the first hollow cylindrical element 1 can be deformed. The deformation is obtained by locking the distal end 1C of the first hollow cylindrical element 1 by a fixing element 5, that prevents said distal end 1C from moving, and applying to the first hollow cylindrical element 1 an axial thrust that compresses the deformation portion of the first hollow cylindrical member in the direction of the axial thrust so as to place the ribs 2 in the deformed configuration.

Figure 7:
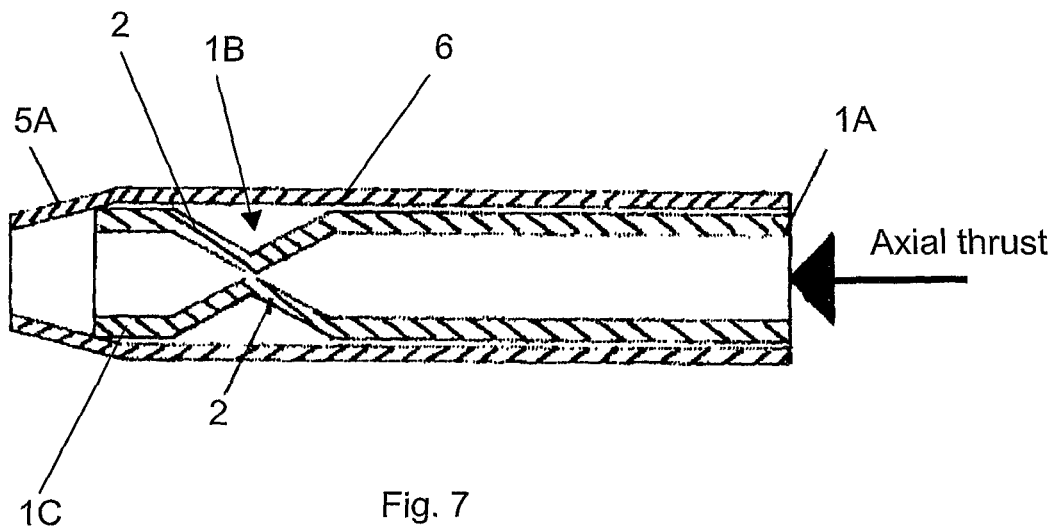

FIG. 7 is a longitudinal section of an embodiment of a biopsy device according to the invention comprising the first hollow cylindrical element 1, inserted inside a second hollow cylindrical element 6, so as to be able to slide in relation thereto. The second hollow cylindrical element 6 is provided with a tapered distal end 5A that constitutes the fixing element that acts as a block to the advancement of the first hollow cylindrical element 1 when an axial thrust is applied thereto that is directed to the distal end 1C thereof; the combined effect of the fixing element 5A and of the axial thrust is to compress the ribs 2 to the deformed configuration to separate a tissue sample from the surrounding tissue and lock the sample tissue inside the first hollow cylindrical element 1.

Figure 8:
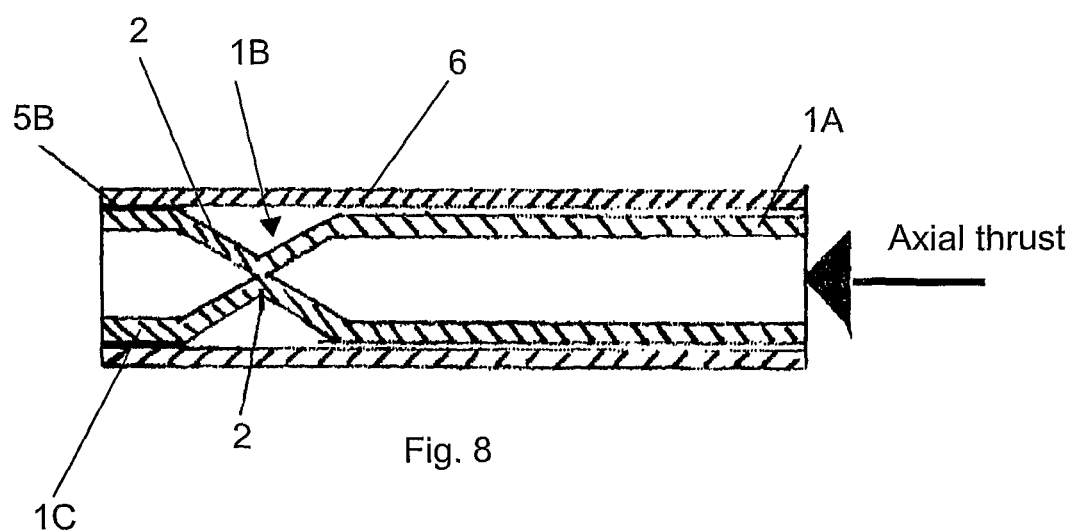

FIG. 8 is a longitudinal section that is similar to that of FIG. 7, that illustrates a further embodiment of a biopsy device according to the invention in which the fixing element consists of a weld 5B by means of which a portion of internal surface of the distal end of the second hollow cylindrical element 6 is welded with a corresponding portion of external surface of the distal end 1C of the first hollow cylindrical element 1. This weld 5B, by preventing the first hollow cylindrical element 1 from sliding axially with respect to the second hollow cylindrical element 6 means that, by applying to the first hollow cylindrical element 1 an axial thrust directed to the distal end 1C thereof, the ribs 2 are compressed to the deformed configuration to separate a tissue sample from the surrounding tissue and lock the tissue sample inside the first hollow cylindrical element 1.

Figure 9:
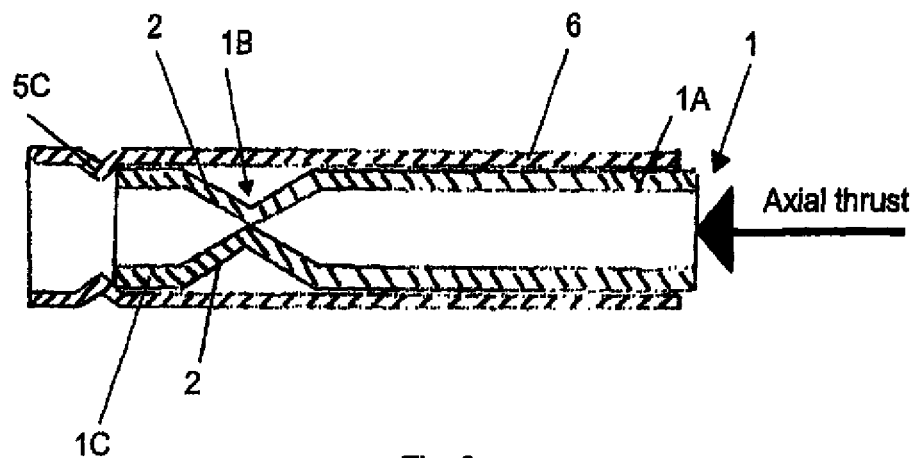

FIG. 9 is a longitudinal section like the one in FIGS. 7 and 8 that illustrates a still further embodiment of a biopsy device according to the invention in which the fixing element consists of a protuberance 5C that protrudes inside the second hollow cylindrical element 6, reducing the cross section thereof locally, so as to constitute a lock to the advancing of the first hollow cylindrical element 1, when axial thrust is applied thereto that is directed to the distal end 1C thereof; the combined effect of the protuberance 5C and of the axial thrust is to compress the ribs 2 to the deformed configuration thereof to separate a tissue sample from the surrounding tissue and lock the tissue sample inside the first hollow cylindrical element 1.

Figure 10:
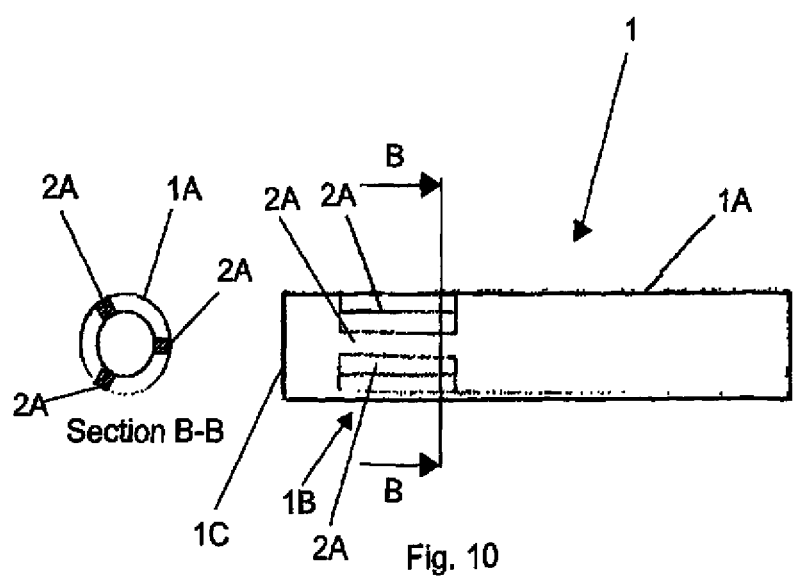

FIG. 10 is a longitudinal and section view like the one in FIG. 2 that illustrates an embodiment of the device according to the invention in which a plurality of ribs 2A is provided, for example three, arranged with a substantially constant angular pitch along the circumference of the first hollow cylindrical element 1, in said deformation portion 1B.

Figure 11:
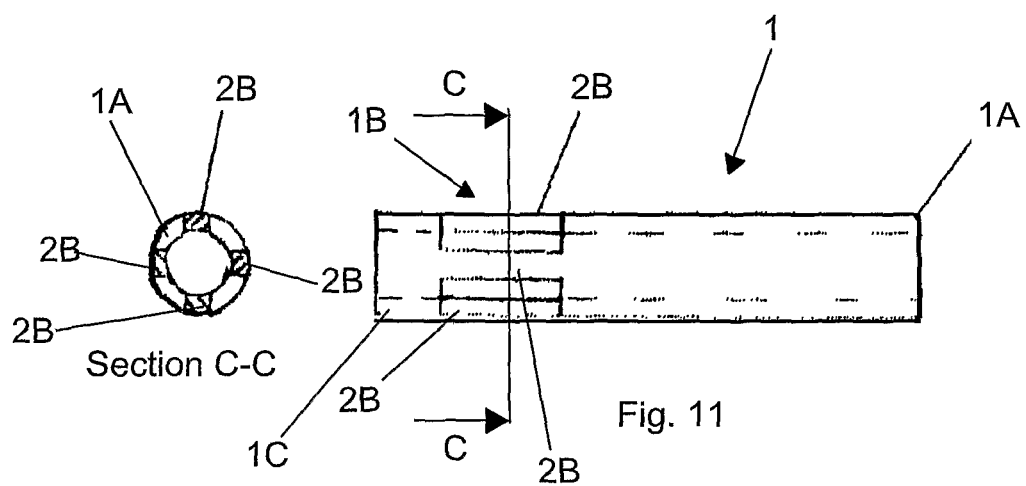

FIG. 11 is a longitudinal and section view like the one in FIG. 10 that illustrates an embodiment of the device according to the invention in which four ribs 2B are provided that are arranged with a substantially constant angular pitch along the circumference of the first hollow cylindrical element 1, in said deformation portion 1B.

Figure 12:
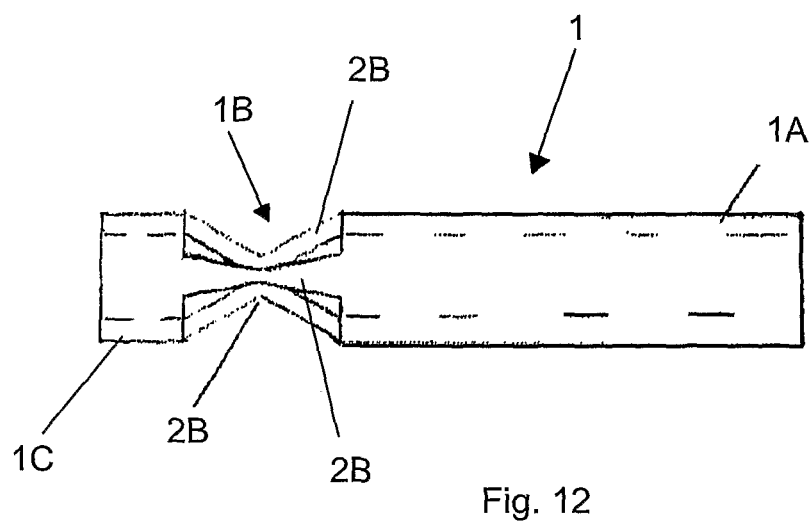

FIG. 12 is a longitudinal view like the one in FIG. 11, illustrating the deformed configuration of the ribs, to separate a tissue sample from the surrounding tissue and lock the tissue sample inside the first hollow cylindrical element;

FIGS. 13, 14, 15 are longitudinal views of the first hollow cylindrical element, showing some possible geometrical shapes of the ribs;

FIGS. 16 to 17 are also longitudinal views of the first hollow cylindrical element, showing some further possible geometries of the ribs, in which at least a pair of ribs are interrupted by a notch; and FIGS. 18 and 19 are views like the one in FIG. 17, which have been rotated by 90° with respect thereto around the longitudinal axis of the first hollow cylindrical element, for showing, respectively, the undeformed configuration and the deformed configuration of the ribs.

Also the geometries of the ribs 2F and 2G illustrated in FIGS. 16 to 19 are given by way of non-limiting example and to illustrate that also the geometry of the ribs even with the presence of notches 7 is not binding to be able to obtain the deformed configuration thereof.

The invention claimed is:

1. A biopsy device, comprising:
   (a) a first hollow cylindrical member including a main body portion, a distal end portion, and a deformable portion arranged between said main body and distal end portions, said deformable portion comprising a plurality of ribs;
   (b) a second hollow cylindrical member being configured to partially house said first hollow cylindrical member and to allow sliding movement of said first hollow cylindrical member relative to said second hollow cylindrical member, said second hollow cylindrical member including a stop configured to block further distal advancement of said distal end portion of said first hollow cylindrical member relative to said second hollow cylindrical member; and
   (c) said ribs being configured to close inwardly to such an extent that opposing portions of said ribs come into contact with each other to detach and lock a tissue sample within said first hollow cylindrical member when an axial thrust is applied against a proximal end of said first hollow cylindrical member while said second hollow cylindrical member is stationary and the axial thrust is applied at least after the distal end portion of said first hollow cylindrical member is blocked from further distal advancement by said stop.

2. A device according to claim 1, wherein said ribs are equally spaced about a circumference of said first hollow cylindrical member.

3. A device according to claim 1, wherein said stop comprises a tapered distal end of said second hollow cylindrical member.

4. A device according to claim 1, wherein said stop comprises a protuberance that protrudes inside said second hollow cylindrical member reducing the cross-section of said second hollow cylindrical member.

5. A biopsy device, comprising:
   (a) a first hollow cylindrical member including a main body portion, a distal end portion, and a deformable portion arranged between said main body and distal end portions, said deformable portion comprising a plurality of ribs;
   (b) a second hollow cylindrical member being configured to partially house said first hollow cylindrical member;
   (c) a weld that connects an internal surface of a distal end portion of said second hollow cylindrical member with a corresponding external surface of the distal end portion of the first hollow cylindrical member; and
   (d) said ribs being configured to close inwardly to such an extent that opposing portions of said ribs come into contact with each other to detach and lock a tissue sample within said first hollow cylindrical member when an axial thrust is applied against a proximal end of said first hollow cylindrical member to displace a proximal portion of said first hollow cylindrical member relative to said second hollow cylindrical member while said second hollow cylindrical member is stationary and the axial thrust is applied after the distal end portion of said first hollow cylindrical member is blocked from distal advancement by said weld.

6. A device according to claim 5, wherein said ribs are equally spaced about a circumference of said first hollow cylindrical member.

* * * * *